US00PP30912P2

(12) United States Plant Patent
Meilland

(10) Patent No.: US PP30,912 P2
(45) Date of Patent: Oct. 1, 2019

(54) LANDSCAPE SHRUB ROSE PLANT NAMED 'MEIRIFTDAY'

(50) Latin Name: *Rosa hybrida*
Varietal Denomination: MEIRIFTDAY

(71) Applicant: THE CONARD-PYLE COMPANY, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,710

(22) Filed: Apr. 12, 2018

(51) Int. Cl.
*A01H 5/02* (2018.01)
*A01H 6/74* (2018.01)

(52) U.S. Cl.
USPC ..... Plt./107
CPC ..... *A01H 6/74* (2018.05)

(58) Field of Classification Search
USPC ..... Plt./107
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct variety of Landscape Shrub Rose plant, herein referred to by its cultivar name, 'MEIRIFTDAY', is provided which forms very abundantly on a nearly continuous basis attractive, flat cup-shaped, dark pink colored blossoms. Attractive, glossy, dense foliage is formed, which contrasts beautifully with the blossoms. The disease tolerance is good, particularly against Black Spot. The new variety is well suited for proving attractive ornamentation in the landscape and is very floriferous.

2 Drawing Sheets

Figure 1:
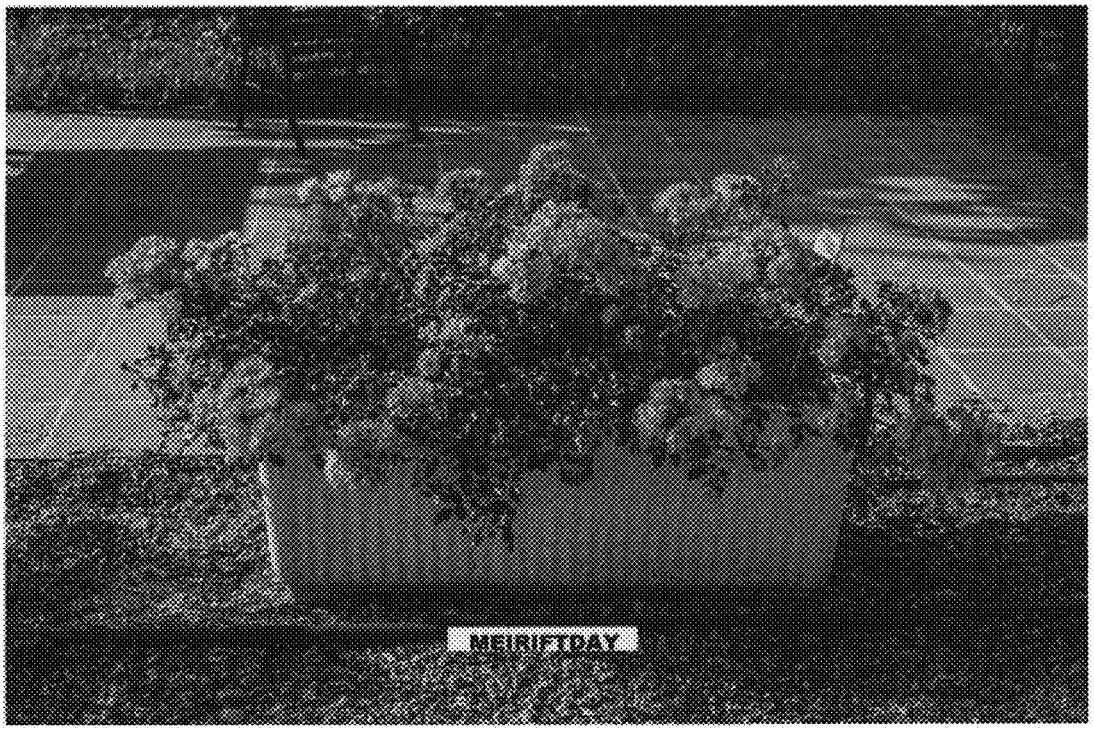

Botanical/commercial classification:
Latin name—*Rosa hybrida.*
Common name—Landscape Shrub Rose Plant.
Varietal denomination—'MEIRIFTDAY'.

SUMMARY OF THE INVENTION

The new variety of *Rosa hybrida* Landscape Shrub Rose plant was created by artificial pollination wherein two parents were crossed which previously had been studied in the hope that they would contribute the desired characteristics. The female parent (i.e., the seed parent) was the 'KORIMRO' variety (non-patented in the United States). The male parent (i.e., the pollen parent) was an unnamed seedling variety (non-patented in the United States).

The parentage of the new variety can be summarized as follows:

'KORIMRO' x 'UNNAMED SEEDLING'

The seeds resulting from the above pollination were sown and small plants were obtained which were physically and biologically different from each other. Selective study resulted in the identification of a single plant of the new variety.

It was found that the new variety of Landscape Shrub Rose plant of the present invention possesses the following combination of characteristics:

(a) very abundantly and nearly continuously forms attractive, flat cup-shaped, dark pink colored blossoms,
(b) forms attractive, dense, glossy foliage,
(c) exhibits good tolerance to diseases, particularly against Black Spot,
(d) is very floriferous, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORIMRO' variety (i.e., the seed parent) exhibits light pink colored blossoms, whereas the new variety exhibits dark pink colored blossoms. In addition, the male parent, the 'UNNAMED SEEDLING' variety, (i.e., the pollen parent) exhibits yellow colored flowers, whereas the new variety exhibits dark pink colored flowers. Moreover, the new variety can be readily distinguished from other similar non-parental varieties. For example, the 'MEIJOCOS' variety (U.S. Plant Pat. No. 18,874) provides a lower petal count compared to the new variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEIRIFTDAY'.

BRIEF DESCRIPTION OF THE PHOTOGRAPH

The accompanying photographs show as nearly true as it is reasonably possible to make the same, in a color illustration of this character, typical specimens of the plant parts of the new variety. The rose plants of the new variety were approximately two years of age and were observed during November while budded on their own roots and growing outdoors at Le Cannet des Maures, Var, France.

FIG. 1—illustrates a specimen of a plant while growing in a pot, which shows the floriferous characteristics of the variety.

Figure 2:
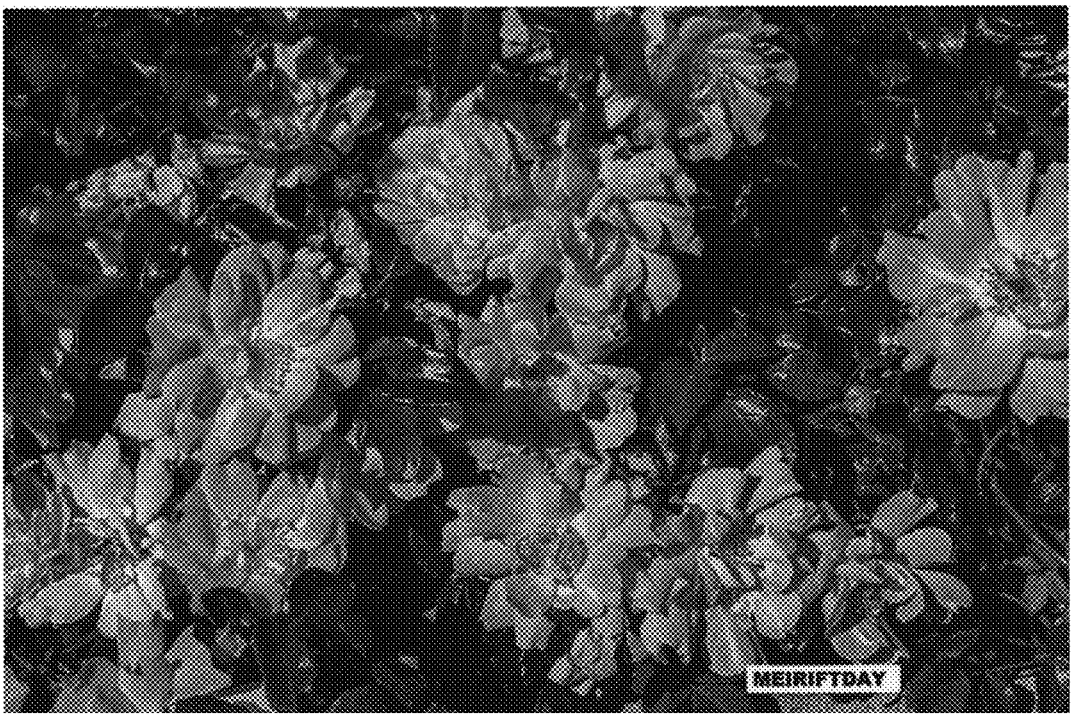

FIG. 2—illustrates a specimen of a plant while growing in a pot, which shows the detail of the flower and foliage.

DETAILED BOTANICAL DESCRIPTION

The chart used in the identification of the colors is that of The Royal Horticultural Society (R.H.S. Colour Chart), London, England. The terminology which precedes reference to the chart has been added to indicate the corresponding color in more common terms. The description is based on the observation of two-year-old specimens of the new variety during November while budded on their own roots and growing outdoors at Le Cannet des Maures, Var, France.

Class: Landscape Shrub Rose Plant.

Plant:

*Habit*.—Bushy.

*Height*.—Approximately 40 cm on average.

*Diameter*.—Approximately 50 cm on average.

Branches:

*Size*.—Length: typically between 15 cm to 30 cm. Diameter: typically between 0.2 cm to 0.5 cm.

*Color*.—Young stems: commonly near Yellow-Green Group 146B. Adult wood: commonly near Yellow-Green Group 146A.

*Thorns*.—Configuration on adult stems: elongated and curved downwards on the upper surface and concave on the under surface. Long prickles (≥0.4 cm) — quantity: commonly approximately 8 thorns per 10 cm long young stem and approximately 5 thorns per 10 cm long adult stem. Long prickles (≥0.4 cm) — base shape: oval. Long prickles (≥0.4 cm) — size: commonly near 0.4 cm in length on average on young stems and commonly near 0.6 cm in length on average on adult stems. Long prickles (≥0.4 cm) — color: commonly near Greyed-Red Group 182B on young stems and commonly near Greyed-Orange Group 173A on adult stems. Small prickles (<0.4 cm): none observed.

Foliage:

*General appearance*.—Dense with a glossy aspect.

*Number of leaflets*.—3, 5, and 7; most often 7.

*Terminal leaflet*.—Length: approximately 3.0 cm on average. Width: approximately 2.5 cm on average.

*New foliage*.—Upper surface color: commonly near Green Group 137C. Under surface color: commonly near Yellow-Green Group 147C.

*Adult foliage*.—Upper surface color: commonly near Yellow-Green Group 147A. Under surface color: commonly near Yellow-Green Group 146B.

*Entire leaf*.—Length: typically between 6 cm to 8 cm. Width: typically between 3.5 cm to 5.5 cm.

Leaflets:

*Shape*.—Tip: obtuse. Base: cupsidate.

*Texture*.—Leathery.

*General appearance*.—Oval.

*Edge*.—Slightly denticulate.

*Serration*.—Small and single.

*Petiole rachis*.—Length: typically between 2.5 cm to 3.5 cm. Diameter: approximately 0.1 cm on average. Color of upper surface: commonly near Yellow-Green Group 146A. Color of under surface: commonly near Yellow-Green Group 146B.

*Petioles*.—Upper surface: no glandular. Under surface: few prickles. Color of upper surface: commonly near Yellow-Green Group 146A. Color of under surface: commonly near Yellow-Green Group 146B. Length: typically between 1.5 cm to 2.0 cm. Diameter: approximately 0.1 cm on average. Petiole length of terminal leaflet: commonly near 2.5 cm on average. Petiole diameter of terminal leaflet: approximately 0.1 cm on average.

*Stipules*.—General appearance: adnate, pectinate and broad. Length: approximately 0.8 cm on average. Width: approximately 1.0 cm on average. Color of upper surface: commonly near Yellow-Green Group 146D. Color of under surface: commonly near Yellow-Green Group 146B.

Inflorescence:

*Number of flowers per stem*.—Generally between 3 and 14 flowers per stem.

*Lastingness of the bloom*.—Commonly between 10 to 15 days.

*Bud*.—Shape: conical. Size: small. Length: approximately 1.5 cm on average. Width: approximately 1.0 cm on average. Color as calyx breaks: Upper surface: commonly near Red Group 53D. Under surface: commonly near Red Group 50A.

*Sepals*.—Number: commonly 5. Length: approximately between 1.9 cm on average. Width: approximately near 0.7 cm on average. Shape: typically between 2 and 5 little glandular extensions, which are approximately 0.5 cm in length on average, at the top: elongated, at the base: upright. Upper surface: Texture: tomentous. Color: commonly near Yellow-Green Group 146D. Under surface: Texture: smooth. Color: commonly near Yellow-Green Group 148D.

*Receptacle*.—Color commonly near Yellow-Green Group 146D. Length: approximately 0.7 cm on average. Width: approximately 0.6 cm on average. Surface: smooth. Shape: pitcher shaped.

*Peduncle*.—Length: approximately 3.2 cm on average. Width: approximately 0.5 cm on average. Surface: pubescent. Color: commonly near Yellow-Green Group 146D.

*Flower*.—Average diameter when fully open: Approximately 5.0 to 6.0 cm on average. Depth: typically between 1.5 cm to 2.0 cm. Borne: commonly between 3 to 14 flowers per stem. Shape: flat cup shaped. Number of petals under normal conditions: approximately 20 to 24 petals on average. Shape of the petal: triangular shape. Base: obtuse. Top: rounded. Petal margin: undulated and become edged when ageing. Texture of the petal: leathery. Petal length: approximately 3.2 cm on average. Petal width: approximately 2.9 cm on average. Petal arrangement: imbricated with some petaloids. Petal drop: petals drop off cleanly before drying. Fragrance: none. Color when opening: Upper surface: commonly near Red-Purple Group 57C, very little spot at the base commonly near Yellow Group 2B. Under surface: commonly near Red-Purple Group 57D, very little spot at the base commonly near Yellow Group 2B. Color of the open flower: Upper surface: commonly near Red-Purple Group 58D amply suffused with near Red-Purple Group 57C, very little spot at the base commonly near Yellow Group 2B. Under surface: commonly near Red-Purple Group 58B amply suffused with near Red-Purple Group 57C, very little spot at the base commonly near Yellow Group 2B. Anthers: number is approximately 68 on average, length is approximately 0.1 cm on average, coloration is commonly near Yellow-Orange Group 15A, and arrangement is regular around styles. Filaments: length is approximately near 0.2 cm on average and coloration is commonly near Yellow Group 2D. Styles: length is approximately 0.2 cm on average, the coloration is commonly near Yellow Group 2D, and the number is approximately 28 on average. Stigmas: size is approximately 0.1 cm on average and the coloration is commonly near Yellow Group 2D. Pollen: not available at this stage. Hips: size is approximately 1.0 cm on average, the shape is rounded, and the coloration is commonly near Red Group 53C.

Development:

*Vegetation*.—Strong.

*Blooming*.—Early in the season, typically May to November, very abundant and nearly continuous.

*Tolerance to disease*.—Good, and particularly against Black Spot.

The new 'MEIRIFTDAY' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Landscape Shrub Rose plant characterized by the following combination of characteristics:

(a) very abundantly and nearly continuously forms attractive, flat cup-shaped, dark pink colored blossoms, (b) forms attractive, dense, glossy foliage, (c) exhibits good tolerance to diseases, particularly against Black Spot, (d) is very floriferous, and (e) is well suited for providing attractive ornamentation; substantially as herein shown and described.

* * * * *